(12) United States Patent
Muslehiddinoglu et al.

(10) Patent No.: US 11,332,489 B2
(45) Date of Patent: May 17, 2022

(54) PROCESS FOR PREPARING IMETELSTAT

(71) Applicant: Geron Corporation, Menlo Park, CA (US)

(72) Inventors: Jale Muslehiddinoglu, Beerse (BE); Dinesh Gala, Beerse (BE); Jennifer Elizabeth Albaneze-Walker, Beerse (BE)

(73) Assignee: Geron Corporation, Foster City, CA (US)

( * ) Notice: Subject to any disclaimer, the term of this patent is extended or adjusted under 35 U.S.C. 154(b) by 0 days.

(21) Appl. No.: 16/623,984

(22) PCT Filed: Jul. 9, 2018

(86) PCT No.: PCT/EP2018/068485
§ 371 (c)(1),
(2) Date: Dec. 18, 2019

(87) PCT Pub. No.: WO2019/011829
PCT Pub. Date: Jan. 17, 2019

(65) Prior Publication Data
US 2020/0369702 A1    Nov. 26, 2020

(30) Foreign Application Priority Data
Jul. 10, 2017  (EP) ..................... 17180426

(51) Int. Cl.
*C07H 1/00* (2006.01)
*C07H 21/04* (2006.01)

(52) U.S. Cl.
CPC ............. *C07H 1/00* (2013.01); *C07H 21/04* (2013.01)

(58) Field of Classification Search
CPC ................... C07H 1/00; C07H 21/04
See application file for complete search history.

(56) References Cited

U.S. PATENT DOCUMENTS

| | | | |
|---|---|---|---|
| 7,494,982 B2 | 2/2009 | Gryaznov et al. | |
| 8,980,853 B2 | 3/2015 | Bennett et al. | |

FOREIGN PATENT DOCUMENTS

| | | | | |
|---|---|---|---|---|
| WO | WO0118015 A1 | 3/2001 | | |
| WO | WO2005023994 | 3/2005 | | |
| WO | WO-2005023994 A2 | * 3/2005 | ..... | C12Y 207/07049 |
| WO | WO2006014387 | 2/2006 | | |
| WO | WO2017223258 | 12/2017 | | |

OTHER PUBLICATIONS

Jensen et al., Biochemistry, 2018, 57, p. 1821-1832. (Year: 2018).*
Lee et al., Nucleic Acids Research, 2010, 38(8), p. 2514-2521. (Year: 2010).*
Horie et al., Nucleic Acids Symposium Series, 2005, 49(1), pp. 171-172. (Year: 2005).*
Herbert, et al., (2005), "Lipid modification of GRN163, an N3'→P5' thio-phosphoramidate oligonucleotide, enhances the potency of telomerase inhibition", Oncogene, vol. 24, pp. 5262-5268.
Scotson, et al., (2016), "Phosphorothioate anti-sense oligonucleotides: the kinetics and mechanism of the sulfurisation of phosphites by phenylacetyl disulfide (PADS).", Organic & Biomolecular Chemistry, vol. 14, No. 46, pp. 10840-10847.

* cited by examiner

*Primary Examiner* — Jonathan S Lau
(74) *Attorney, Agent, or Firm* — Rudy J. Ng; Bozicevic, Field & Francis LLP

(57) ABSTRACT

The present invention relates to a process for preparing the telomerase inhibitor imetelstat using a 3 steps per cycle phase support bound process comprising the steps of deprotection of the 3'-amino group of the support-bound oligonucleotide, coupling with a 5'-phosphoramidite, and sulfurization with an acyl disulfide, characterized by the absence of an additional capping step in each cycle that is used to prevent unreacted 3'-amino oligonucleotide groups from reacting during subsequent cycles. Imetelstat has formula below.

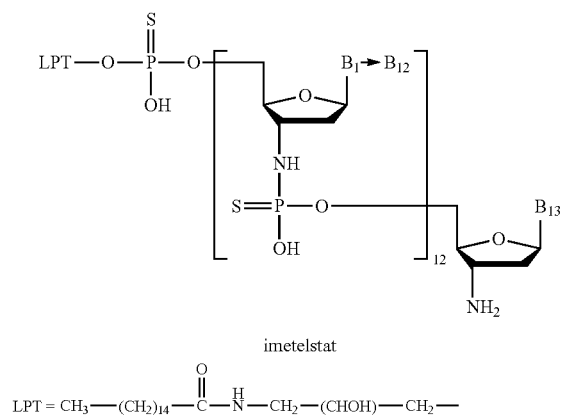

imetelstat $LPT = CH_3-(CH_2)_{14}-\overset{O}{\overset{\|}{C}}-\overset{H}{\overset{|}{N}}-CH_2-(CHOH)-CH_2-$ $B_1 = T$
$B_2 = A$
$B_3 = G$
$B_4 = G$
$B_5 = G$
$B_6 = T$
$B_7 = T$
$B_8 = A$
$B_9 = G$
$B_{10} = A$
$B_{11} = C$
$B_{12} = A$
$B_{13} = A$
T = thymine
A = adenine
G = guanine
C = cytosine

13 Claims, No Drawings
Specification includes a Sequence Listing.

SEQUENCE LISTING

<160> NUMBER OF SEQ ID NOS: 1

<210> SEQ ID NO 1
<211> LENGTH: 13
<212> TYPE: DNA
<213> ORGANISM: Artificial sequence
<220> FEATURE:
<223> OTHER INFORMATION: synthetic sequence

<400> SEQUENCE: 1
tagggttaga caa

PROCESS FOR PREPARING IMETELSTAT

The present invention relates to a process for preparing the telomerase inhibitor imetelstat using a 3 steps per cycle solid-phase support bound process comprising the steps of deprotection of the 3'-amino group of the support-bound oligonucleotide, coupling with a 5'-phosphoramidite, and sulfurization with an acyl disulfide, characterized by the absence of an additional capping step in each cycle that is used to prevent unreacted 3'-amino oligonucleotide groups from reacting during subsequent cycles.

BACKGROUND

Imetelstat (SEQ ID NO:1) is a N3'→P5' thiophosphoramidate oligonucleotide covalently linked to a palmitoyl lipid moiety and has been described in WO-2005/023994 as compound (1F). The sodium salt of imetelstat acts as a potent and specific telomerase inhibitor and can be used to treat telomerase-mediated disorders, e.g. cancer, including disorders such as myelofibrosis (MF), myelodysplastic syndromes (MDS) and acute myelogenous leukemia (AML).

The structure of imetelstat sodium is shown below:

The structure of imetelstat can also be represented as shown below

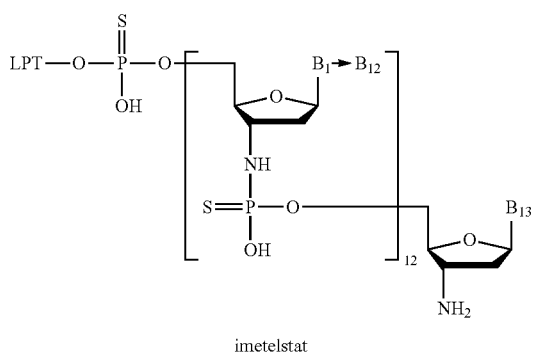

imetelstat

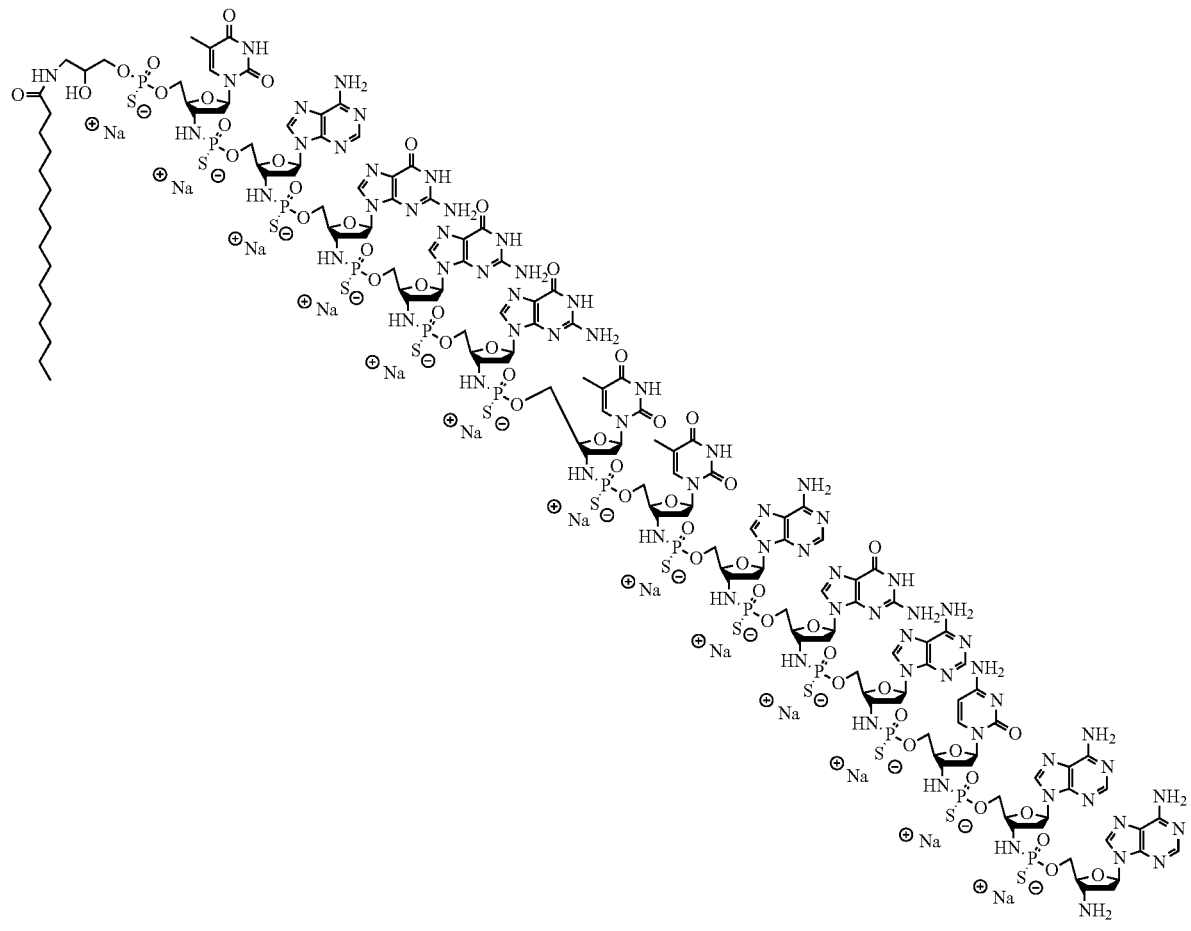

imetelstat sodium

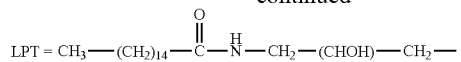

$B_1 = T$
$B_2 = A$
$B_3 = G$
$B_4 = G$
$B_5 = G$
$B_6 = T$
$B_7 = T$
$B_8 = A$
$B_9 = G$
$B_{10} = A$
$B_{11} = C$
$B_{12} = A$
$B_{13} = A$
T = thymine
A = adenine
G = guanine
C = cytosine The LPT group represents the palmitoyl lipid that is covalently linked to the N3'→P5' thiophosphoramidate oligonucleotide. The base sequence of the thirteen nucleotides is as follows:
TAGGGTTAGACAA and is represented by the bases $B_1$ to $B_{13}$. The —NH—P(=S)(OH)— and —O—P(=S)(OH)— groups of the structure can occur in a salt form. It is understood that salt forms of a subject compound are encompassed by the structures depicted herein, even if not specifically indicated.

Imetelstat sodium can also be represented as follows:

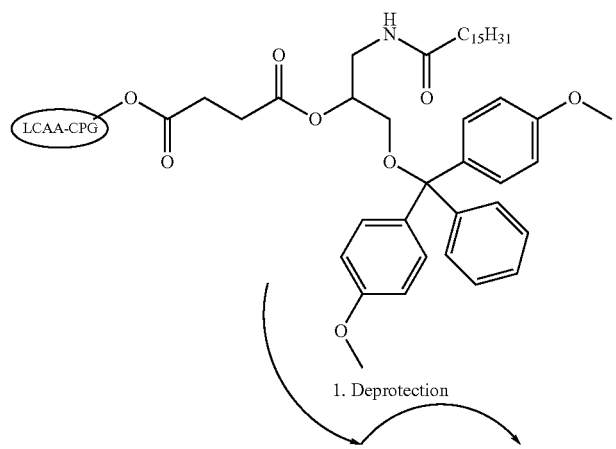

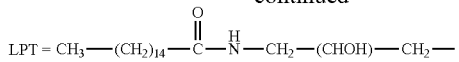

$B_1 = T$
$B_2 = A$
$B_3 = G$
$B_4 = G$
$B_5 = G$
$B_6 = T$
$B_7 = T$
$B_8 = A$
$B_9 = G$
$B_{10} = A$
$B_{11} = C$
$B_{12} = A$
$B_{13} = A$
T = thymine
A = adenine
G = guanine
C = cytosine The —NH—P(=S)(OH)— group and the thymine, adenine, guanine and cytosine bases can occur in other tautomeric arrangements then used in the figures of the description. It is understood that all tautomeric forms of a subject compound are encompassed by a structure where one possible tautomeric form of the compound is described, even if not specifically indicated.

PRIOR ART

The synthetic scheme used in WO-2005/023994 to prepare imetelstat as compound (1F) is described in Scheme 1 and Scheme 2. The synthesis of this oligonucleotide is achieved using the solid-phase phosphoramidite methodology with all reactions taking place on solid-phase support. The synthesis of imetelstat is carried out on controlled pore glass (LCAA-CPG) loaded with 3-palmitoylamido-1-O-(4, 4'-dimethoxytrityl)-2-O-succinyl propanediol. The oligonucleotide is assembled from the 5' to the 3' terminus by the addition of protected nucleoside 5'-phosphoramidites with the assistance of an activator. Each elongation cycle consists of 4 distinct, highly controlled steps: deprotection, amidite coupling, sulfurization and a capping step.

Scheme 1: imetelstat synthetic scheme cycle 1

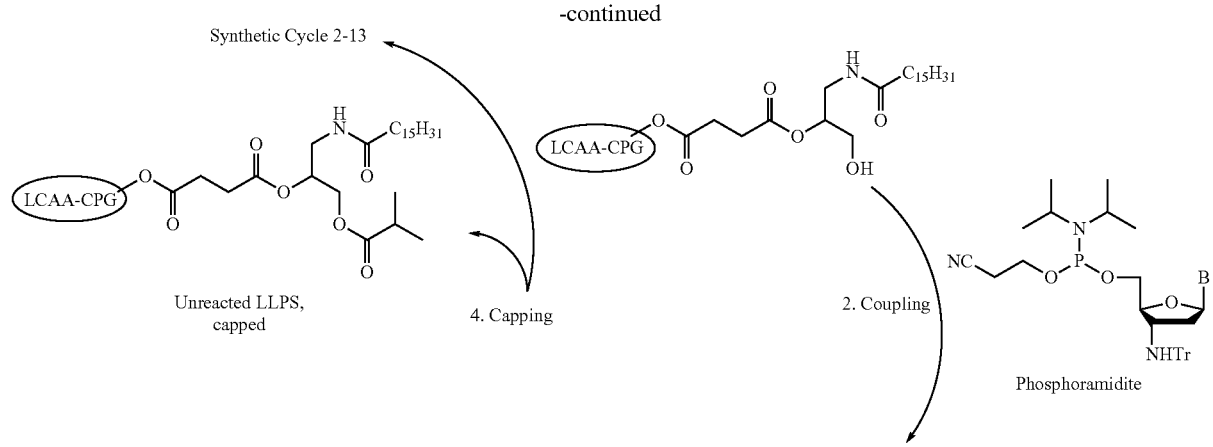

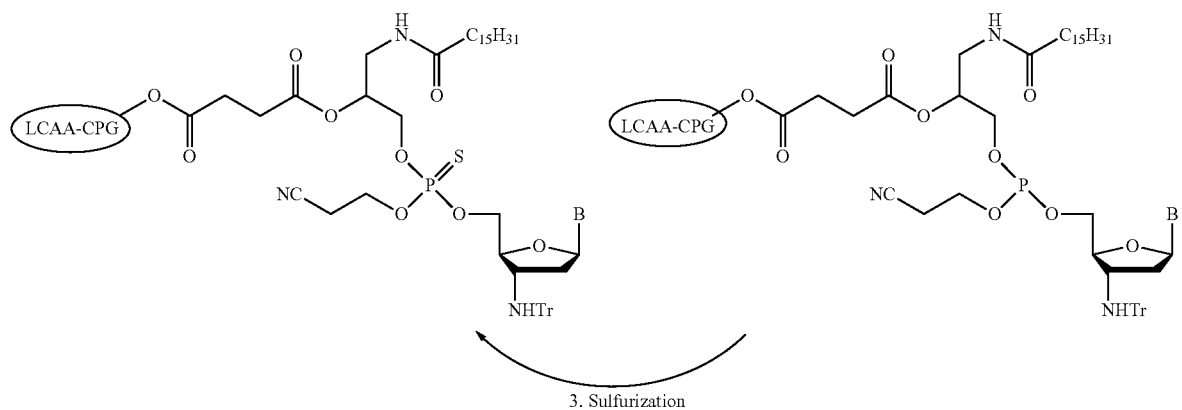

In Scheme 1 the solid-phase supported synthesis starts with removal of the acid-labile 4,4-dimethoxytrityl (DMT) protecting group from the palmitoylamidopropanediol linked to the solid-phase support. The first phosphoramidite nucleotide is coupled to the support followed by sulfurization of the phosphor using a 0.1 M solution of phenylacetyl disulfide (PADS) in a mixture of acetonitrile and 2,6-lutidine (1:1 ratio). Then a capping step is applied to prevent any unreacted solid-phase support starting material from coupling with a phosphoramidite nucleotide in the following reaction cycles. Capping is done using an 18:1:1 mixture of THF/isobutyric anhydride/2,6-lutidine.

After the first cycle on the solid-phase support, chain elongation is achieved by reaction of the 3'-amino group of the support-bound oligonucleotide with an excess of a solution of the protected nucleotide phosphoramidite monomer corresponding to the next required nucleotide in the sequence as depicted in Scheme 2.

Scheme 2: imetelstat synthetic scheme cycle 2-13

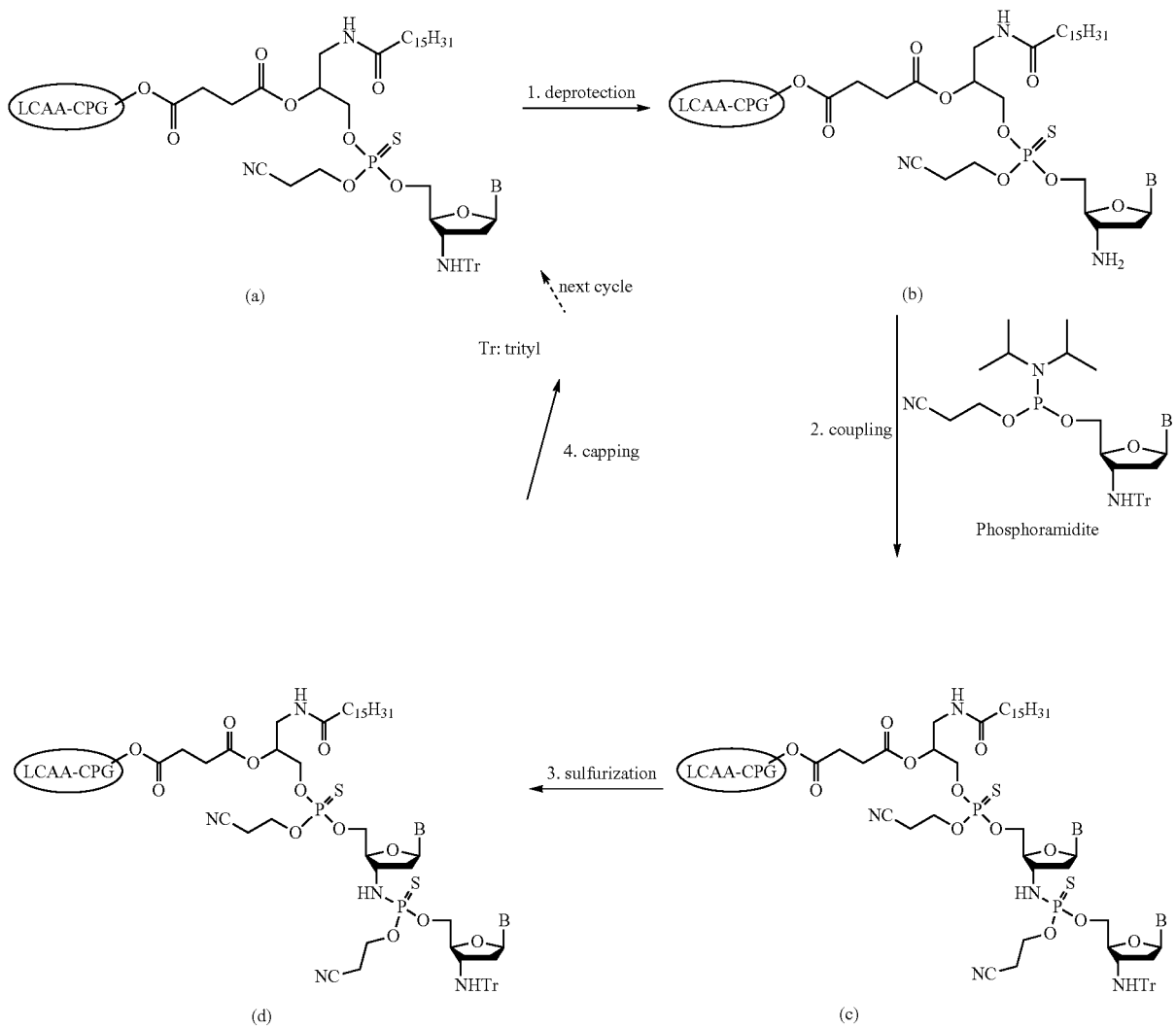

Tr: trityl

In Scheme 2 the first cycle is depicted of the chain elongation process which is achieved by deprotection of the 3'-amino group of the support-bound oligonucleotide (a), followed by a coupling reaction of the 3'-amino group of the support-bound oligonucleotide (b) with an excess of a solution of a 5'-phosphoramidite monomer corresponding to the next required nucleotide in the sequence of imetelstat. The coupling reaction is followed by sulfurization of the phosphor of the support-bound oligonucleotide (c) and a capping step (see Scheme 3) to prevent any unreacted solid-phase support starting material (b) from coupling with a 5'-phosphoramidite nucleotide in the following reaction cycles. The reaction cycle of Scheme 2 is repeated 12 times before the solid-phase support-bound oligonucleotide is treated with a 1:1 mixture of ethanol and concentrated ammonia, followed by HPLC purification to obtain imetelstat.

Scheme 3

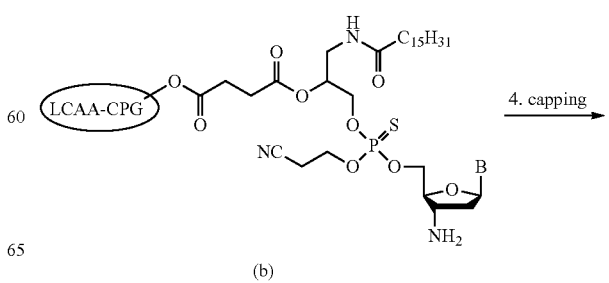

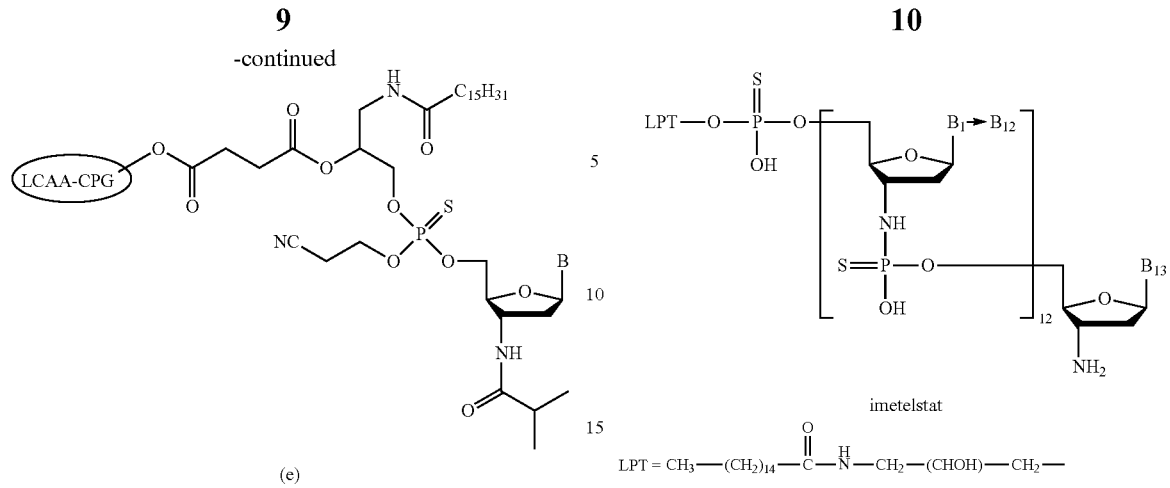

(e)

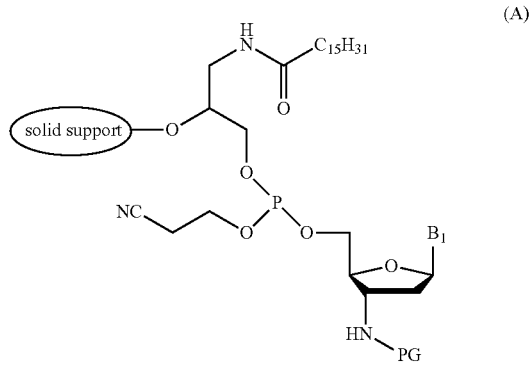

imetelstat $$LPT = CH_3-(CH_2)_{14}-\overset{O}{\underset{\|}{C}}-\overset{H}{\underset{|}{N}}-CH_2-(CHOH)-CH_2-$$

$B_1 = T$
$B_2 = A$
$B_3 = G$
$B_4 = G$
$B_5 = G$
$B_6 = T$
$B_7 = T$
$B_8 = A$
$B_9 = G$
$B_{10} = A$
$B_{11} = C$
$B_{12} = A$
$B_{13} = A$
T = thymine
A = adenine
G = guanine
C = cytosine The capping step using an 18:1:1 mixture of THF/isobutyric anhydride/2,6-lutidine is done to convert after the coupling step any remaining solid-phase support bound oligonucleotide (b) with a primary 3'-amino group into oligonucleotide (e) with a protected (or 'capped') 3'-amino group in order to prevent the primary 3'-amino group from coupling with a phosphoramidite nucleotide in the next reaction cycles.

WO-01/18015 discloses in Example 3 with SEQ ID No. 2 a N3'→P5' thiophosphoramidate oligonucleotide and a process for preparing this oligonucleotide encompassing a capping step.

DESCRIPTION OF THE INVENTION

The coupling reaction in the solid-phase support bound process disclosed in WO-01/18015 and WO-2005/023994 include a capping step to prevent any unreacted primary 3' amino groups on the support-bound oligonucleotide from reacting during subsequent cycles.

It has now surprisingly been found that the use of a capping step as described in the prior art is superfluous and that imetelstat can be prepared using a 3-step cycle without an additional capping step with nearly identical yield and purity compared to the prior art 4-step cycle that uses a specific capping step. Eliminating the capping step from each cycle benefits the overall process by reducing the number of cycle steps by 22% (from 54 to 42 steps) and consequent reduction of process time. Also, the solvent consumption is reduced due to the reduction of cycle steps which makes for a greener process.

Wherever the term "capping step" is used throughout this text, it is intended to define an additional chemical process step wherein the primary free 3'-amino group on the solid-phase support bound oligonucleotide is converted into a substituted secondary or tertiary 3'-amino group that is not capable of participating in the coupling reaction with a protected 3'-aminonucleoside-5-O-cyanoethyl-N,N-diisopropylamino-phosphoramidite monomer in the ensuing coupling step.

In one embodiment, the present invention relates to a method of synthesizing an oligonucleotide N3'→P5' thiophosphoramidate of formula the method comprises of a) providing a first 3'-amino protected nucleotide attached to a solid-phase support of formula (A) wherein PG is an acid-labile protecting group;

(A)

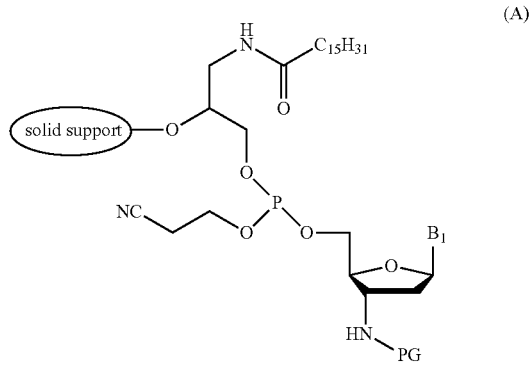

b) deprotecting the protected 3'-amino group to form a free 3'-amino group;

(A')

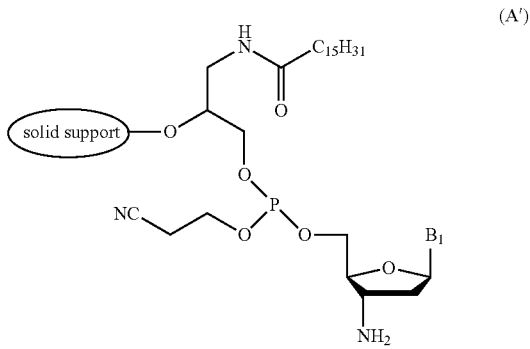

c) reacting the free 3'-amino group with a protected 3'-aminonucleoside-5'-O-cyanoethyl-N,N-diisopropylaminophosphoramidite monomer of formula (B'$_n$) wherein n=2 to form an internucleoside N3→P5'-phosphoramidite linkage;

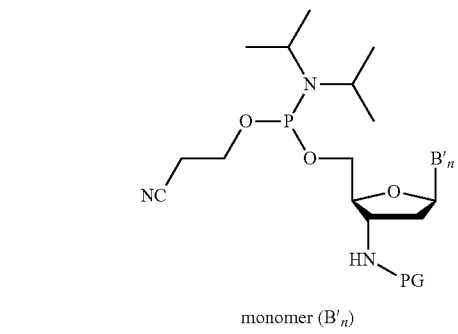

monomer (B'$_n$)

n = 2 d) sulfurization of the internucleoside phosphoramidite group using an acyl disulfide to form a N3'→P5' thiophosphoramidate;
e) repeating 11 times in successive order the deprotection step b), the coupling step c) with a protected 3'-aminonucleoside-5-O-cyanoethyl-N,N-diisopropylaminophosphoramidite monomer of formula (B'$_n$) wherein the protected nucleoside base B' in monomer (B'$_n$) is successively the protected nucleobase B$_3$ to B$_{13}$ in the respective 11 coupling steps, and the sulfurization step d);
f) removing the acid-labile protecting group PG; and
g) cleaving and deprotecting imetelstat from the solid-phase support;

characterized in that no additional capping step is performed in any of the reaction steps a) to e).

A wide variety of solid-phase supports may be used with the invention, including but not limited to, such as microparticles made of controlled pore glass (CPG), highly cross-linked polystyrene, hybrid controlled pore glass loaded with cross-linked polystyrene supports, acrylic copolymers, cellulose, nylon, dextran, latex, polyacrolein, and the like.

The 3'-amino protected nucleotide attached to a solid-phase support of formula (A)

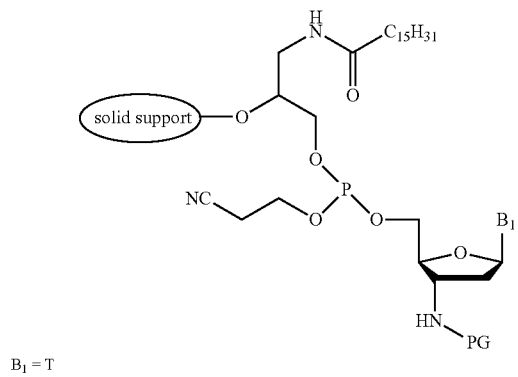

B$_1$ = T can be prepared as disclosed in WO-2005/023994 wherein a controlled pore glass support loaded with 3-palmitoylamido-1-O-(4, 4'-dimethoxytrityl)-2-O-succinyl propanediol has been coupled with a protected 3'-aminonucleoside-5'-O-cyanoethyl-N,N-diisopropylaminophosphoramidite monomer of formula (B'$_1$)

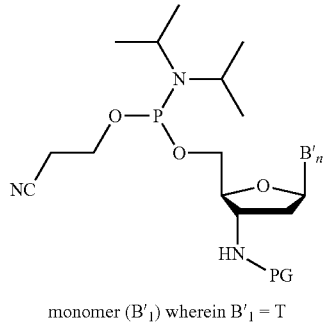

monomer (B'$_1$) wherein B'$_1$ = T wherein PG is an acid-labile protecting group. Suitable acid-labile 3'-amino protecting groups PG are, but not limited to, e.g. triphenylmethyl (i.e. trityl or Tr), p-anisyldiphenylmethyl (i.e. monomethoxytrityl or MMT), and di-p-anisylphenylmethyl (i.e. dimethoxytrityl or DMT).

The protected 3'-aminonucleoside-5'-O-cyanoethyl-N,N-diisopropylaminophosphoramidite monomers of formula (B'$_n$) have a 3'-amino protecting group PG which is an acid-labile group, such as triphenylmethyl (i.e. trityl or Tr), p-anisyldiphenylmethyl (i.e. monomethoxytrityl or MMT), or di-p-anisylphenylmethyl (i.e. dimethoxytrityl or DMT). Furthermore the nucleoside base B' is protected with a base-labile protecting group (except for thymine).

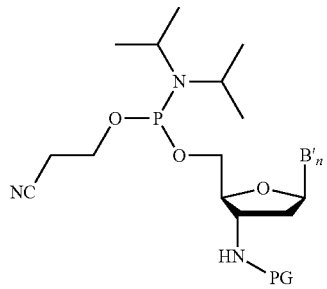

monomer (B'$_n$)

B'$_1$ = T
B'$_2$ = protected A
B'$_3$ = protected G
B'$_4$ = protected G
B'$_5$ = protected G
B'$_6$ = T
B'$_7$ = T
B'$_8$ = protected A
B'$_9$ = protected G
B'$_{10}$ = protected A
B'$_{11}$ = protected C
B'$_{12}$ = protected A
B'$_{13}$ = protected A
T = thymine
A = adenine
G = guanine
C = cytosine The nucleotide monomers and B'$_1$ to B'$_2$ to B'$_{13}$ are used successively in the 13 coupling steps starting from the provision of a solid-phase support loaded with 3-palmitoylamido-1-O-(4, 4'-dimethoxytrityl)-2-O-succinyl propanediol and coupled to nucleotide monomer B'$_1$ and the following cycle of 12 deprotection, coupling, and sulfurization reactions wherein the nucleotide monomers $B'_2$ to $B'_{13}$ are used.

The 3'-amino protecting group PG can be removed by treatment with an acidic solution such as e.g. dichloroacetic acid in dichloromethane or toluene.

The nucleoside base B' in the protected 3'-aminonucleoside-5'-O-cyanoethyl-N,N-diisopropylaminophosphoramidite monomers of formula ($B'_n$) is protected with a base-labile protecting group which is removed in step f). Suitable base-labile protecting groups for the nucleoside base adenine, cytosine or guanine are e.g. acyl groups such as acetyl, benzoyl, isobutyryl, dimethylformamidinyl, or dibenzylformamidinyl. Under the reaction conditions used in oligonucleotide synthesis the thymine nucleoside base does not require protection. Such protected 3'-aminonucleoside-5'-O-cyanoethyl-N,N-diisopropylaminophosphoramidite monomers of formula ($B'_n$) having a 3'-amino protected with an acid-labile group protecting group PG and a nucleoside base B' protected with a base-labile protecting group are commercially available or can be prepared as described in WO-2006/014387.

The coupling step c) is performed by adding a solution of protected 3'-aminonucleoside-5-O-cyanoethyl-N,N-diisopropylaminophosphoramidite monomer of formula ($B_n$) and a solution of an activator (or a solution containing the phosphoramidite monomer ($B_n$) and the activator) to the reaction vessel containing the free amino group of an (oligo)nucleotide covalently attached to a solid support. The mixture is then mixed by such methods as mechanically vortexing, sparging with an inert gas, etc. Alternately, the solution(s) of monomer and activator can be made to flow through a reaction vessel (or column) containing the solid-phase supported (oligo)nucleotide with a free 3'-amino group. The monomer and the activator either can be premixed, mixed in the valve-block of a suitable synthesizer, mixed in a pre-activation vessel and preequilibrated if desired, or they can be added separately to the reaction vessel.

Examples of activators for use in the invention are, but not limited to, tetrazole, 5-(ethylthio)-1H-tetrazole, 5-(4-nitrophenyl)tetrazole, 5-(2-thienyl)-1H-tetrazole, triazole, pyridinium chloride, and the like. Suitable solvents are acetonitrile, tetrahydrofuran, dichloromethane, and the like. In practice acetonitrile is a commonly used solvent for oligonucleotide synthesis.

The sulfurization agent for use in step d) is an acyl disulfide dissolved in a solvent. Art know acyl disulfides are e.g. dibenzoyl disulphide, bis(phenylacetyl) disulfide (PADS), bis(4-methoxybenzoyl) disulphide, bis(4-methylbenzoyl) disulphide, bis(4-nitrobenzoyl) disulphide and bis (4-chlorobenzoyl) disulfide.

Phenylacetyl disulfide (PADS) is a commonly used agent for sulfurization reactions that it is best 'aged' in a basic solution to obtain optimal sulfurization activity (Scotson J. L. et al., Org. Biomol. Chem., vol. 14, 10840-10847, 2016).

A suitable solvent for PADS is e.g. a mixture of a basic solvent such as e.g. 3-picoline or 2,6-lutidine with a co-solvent such as acetonitrile, toluene, 1-methyl-pyrrolidinone or tetrahydrofuran. The amount of the basic solvent to the amount of the co-solvent can be any ratio including a 1:1 ratio. Depending upon the phosphite ester to be converted into its corresponding thiophospate, both 'fresh' and 'aged' PADS can be used however 'aged' PADS has been shown to improve the rate and efficiency of sulfurization. 'Aged' PADS solutions are freshly prepared PADS solutions that were maintained some time before usage in the sulfurization reaction. Aging times can vary from a few hours to 48 hours and the skilled person can determine the optimal aging time by analysing the sulfurization reaction for yield and purity.

For the preparation of imetelstat in accordance with the present invention, a PADS solution in a mixture of acetonitrile and 2,6-lutidine, preferably in a 1:1 ratio, with an aging time of 4 to 14 hours is used.

In step f) imetelstat is deprotected and cleaved from the solid-phase support. Deprotection includes the removal of the β-cyanoethyl groups and the base-labile protecting groups on the nucleotide bases. This can be done by treatment with a basic solution such as a diethylamine (DEA) solution in acetonitrile, followed by treatment with aqueous ammonia dissolved in an alcohol such as ethanol.

The reaction steps a) to e) of the present invention are carried out in the temperature range of 10° C. to 40° C. More preferably, these reactions are carried out at a controlled temperature ranging from 15° C. to 30° C. The step f) wherein imetelstat is deprotected and cleaved from the solid-phase support is carried out at a temperature ranging from 30° C. to 60° C. Depending upon the equipment and the specific reaction conditions used, the optimal reaction temperature for each step a) to f) within the above stated ranges can be determined by the skilled person.

After each step in the elongation cycle, the solid-phase support is rinsed with a solvent, for instance acetonitrile, in preparation for the next reaction.

After step f), crude imetelstat is obtained in its ammonium salt form which is then purified by a preparative reversed phase high performance liquid chromatography (RP-HPLC) by using either polymeric or silica based resins to get purified imetelstat in triethyl amine form. An excess of a sodium salt is added, and then the solution is desalted by diafiltration thereby yielding imetelstat sodium which is then lyophilized to remove water.

EXPERIMENTAL PART

Experiment 1 (No Capping Step)

All the reagents and starting material solutions were prepared including 3% dichloroacetic acid (DCA) in toluene, 0.5 M 5-(ethylthio)-1H-tetrazole in acetonitrile, 0.15 M of all 4 nucleotide monomers of formula ($B'_n$) in acetonitrile, 0.2 M phenyl acetyl disulfide (PADS) in a 1:1 mixture of acetonitrile and 2,6-lutidine and 20% DEA (diethylamine) in acetonitrile.

| nucleotide monomer of formula $(B'_n)$ | Structure |
| --- | --- |
| $B'_1, B'_6, B'_7$ | 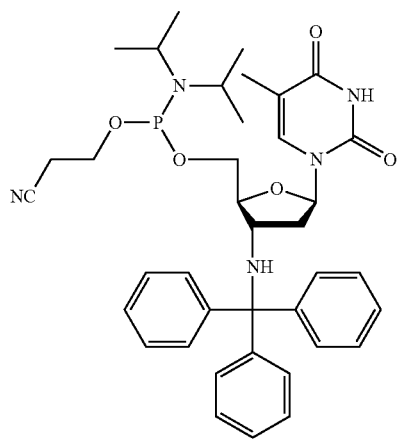 |
| $B'_2, B'_8, B'_{10}, B'_{12}, B'_{13}$ | 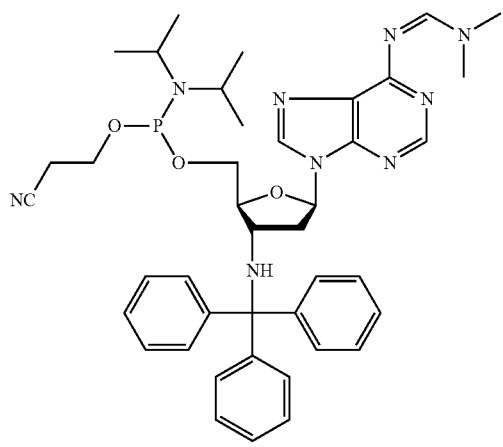 |
| $B'_3, B'_4, B'_5, B'_9$ | 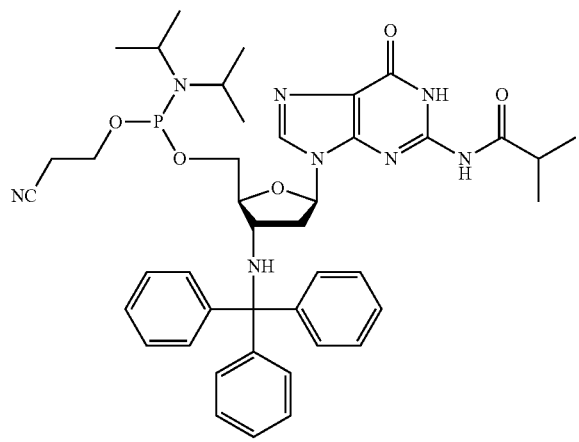 |

| nucleotide monomer of formula (B'$_n$) | Structure |
|---|---|
| B'$_{11}$ | 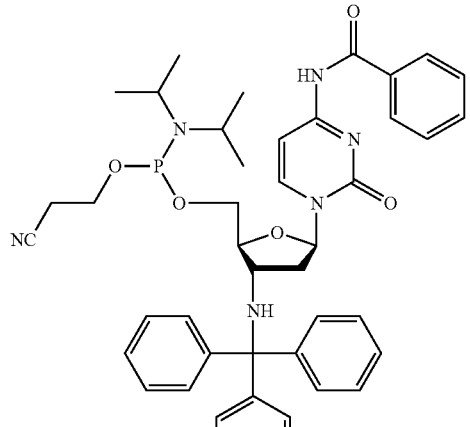 |

The oligonucleotide synthesis was performed in the direction of 5' to 3' utilizing a repetitive synthesis cycle consisting of detritylation followed by coupling, and sulfurization performed at ambient temperature.

A column (diameter: 3.5 cm) was packed with a solid-support loaded with 3-palmitoylamido-1-O-(4,4'-dimethoxytrityl)-2-O-succinyl propanediol (3.5 mmol based on a capacity of 400 μmol/g) that was coupled with the nucleotide monomer B'$_1$. Detritylation was achieved using 3% dichloroacetic acid (DCA) in toluene (amount is between 6.5 and 13.4 column volumes in each detritylation step) and the solid-support bound nucleotide was washed with acetonitrile (amount: 5 column volumes). Coupling with the next nucleotide monomer of formula (B'$_n$) was achieved by pumping a solution of 0.5 M 5-(ethylthio)-1H-tetrazole in acetonitrile and 0.15 M of the next nucleotide monomer of formula (B'$_n$) in the sequence, dissolved in acetonitrile, through the column. The column was washed with acetonitrile (amount: 2 column volumes). Then sulfurization was performed by pumping a solution of 0.2 M phenyl acetyl disulfide (PADS) in a 1:1 mixture of acetonitrile and 2,6-lutidine mixture through the column followed by washing the column with acetonitrile (amount: 5 column volumes).

The synthesis cycle of detritylation, coupling with the next nucleotide monomer of formula (B'$_n$) and sulfurization was repeated 12 times, followed by detritylation using 3% dichloroacetic acid (DCA) in toluene (amount is between 6.5 and 13.4 column volumes).

Upon completion of the synthesis cycle, the crude oligonucleotide on the solid-support support was treated with a diethylamine (DEA) solution followed by treatment with ammonium hydroxide solution:ethanol (3:1 volume ratio) at a temperature of 55° C. The reaction mixture was aged for 4 to 24 hours at 55° C., cooled to room temperature, and slurry was filtered to remove the polymeric support. The solution comprising imetelstat in its ammonium form was subjected to the HPLC analysis procedure of Experiment 3.

Experiment 2 (with Capping Step)

All the reagents and starting material solutions were prepared including 3% dichloroacetic acid (DCA) in toluene, 0.5 M 5-(ethylthio)-1H-tetrazole in acetonitrile, 0.15 M of all 4 nucleotide monomers of formula (B'$_n$) in acetonitrile, 0.2 M phenyl acetyl disulfide (PADS) in a 1:1 mixture of acetonitrile and 2,6-lutidine mixture, 20% N-methylimidazole (NMI) in acetonitrile as capping agent A, isobutryic anhydride in a 1:1 mixture of acetonitrile and 2,6-lutidine mixture as capping agent B and 20% DEA in acetonitrile.

The oligonucleotide synthesis was performed in the direction of 5' to 3' utilizing a repetitive synthesis cycle consisting of detritylation followed by coupling, and sulfurization performed at ambient temperature.

A column (diameter: 3.5 cm) was packed with a solid-support loaded with 3-palmitoylamido-1-O-(4, 4'-dimethoxytrityl)-2-O-succinyl propanediol (3.5 mmol based on a capacity of 400 μmol/g) that was coupled with the nucleotide monomer B'$_1$. Detritylation was achieved using 3% dichloroacetic acid (DCA) in toluene (amount is between 6.5 and 13.4 column volumes in each detritylation step) and the solid-support bound nucleotide was washed with acetonitrile (amount: 5 column volumes). Coupling with the next nucleotide monomer of formula (B'$_n$) was achieved by pumping a solution of 0.5 M 5-(ethylthio)-1H-tetrazole in acetonitrile and 0.15 M of the next nucleotide monomer of formula (B'$_n$) in the sequence, dissolved in acetonitrile, through the column. The column was washed with acetonitrile (amount: 2 column volumes). Then sulfurization was performed by pumping a solution of 0.2 M phenyl acetyl disulfide (PADS) in a 1:1 mixture of acetonitrile and 2,6- lutidine mixture through the column followed by washing the column with acetonitrile (amount: 5 column volumes).

The sulfurization was followed by a capping step. Each capping in a given cycle used 37-47 equivalents (eq.) of the capping agent NMI, and 9-11 equivalents of the capping agent B isobutryic anhydride (IBA), and 1.4-1.8 equivalents of 2,6 lutidine. Capping agents A and B were pumped through the column with separate pumps at different ratios such as 50:50, 35:65, 65:35.

The synthesis cycle of detritylation, coupling with the next nucleotide monomer of formula ($B'_n$) and sulfurization, and capping step was repeated 12 times, followed by detritylation using 3% dichloroacetic acid (DCA) in toluene (amount is between 6.5 and 13.4 column volumes).

Upon completion of the synthesis cycle, the crude oligonucleotide on the solid-support support was treated with a diethylamine (DEA) solution followed by treatment with ammonium hydroxide solution:ethanol (3:1 volume ratio) at a temperature of 55° C. The reaction mixture was aged for 4 to 24 hours at 55° C., cooled to room temperature, and slurry was filtered to remove the polymeric support. The solution comprising imetelstat in its ammonium form was subjected to the HPLC analysis procedure of Experiment 3.

Experiment 3 Comparision of No-Capping vs. Capping

Imetelstat obtained in Experiment 1 and Experiment 2 was analysed by HPLC. The amount of the desired full length oligonucleotide having 13 nucleotides was determined and listed in the Table below for Experiment 1 and Experiment 2. Also, the total amount of shortmer, specifically the 12 mer, was determined and listed in the Table below for Experiment 1 and Experiment 2.

HPLC analysis method:
column type: Kromasil C18, 3.5 μm particle size, 4.6×150 mm
eluent:
A: 14.4 mM TEA/386 mM HFIP (hexafluoroisopropanol)/100 ppm(w/v) $Na_2EDTA$ in water
B: 50% MeOH, 50% EtOH containing 5% IPA
Gradient:

| Step | Run time (minutes) | % B |
|---|---|---|
| 1 | 0 | 10 |
| 2 | 5 | 10 |
| 3 | 12 | 26 (linear) |
| 4 | 35 | 45 (linear) |
| 5 | 40 | 50 (linear) |
| 6 | 42 | 50 |
| 7 | 44 | 10 (linear) |
| 8 | 50 | 10 |

TABLE capping vs. no-capping experiments (Experiment 1 was run twice and results are listed as Experiment 1a and 1b).

| Experiment # | capping or no capping | Full length oligonucleotide | Shortmer (12 mer) |
|---|---|---|---|
| 1a | no capping | 71.6% | 5.5% |
| 1b | no capping | 71.2% | 5.7% |
| 2 | capping | 71.3% | 5.6% |

The HPLC analysis of Experiment 1 and Experiment 2 demonstrates that yield and purity are comparable for the no-capping experiment vs. the capping experiment.

Solvent Use and Reaction Time 0.45 L of acetonitrile/mmol is used to prepare capping agent A and capping agent B reagents which corresponds to approximately 25% of the overall acetonitrile use during the preparation of the reagents. Since each chemical reaction step is followed by a solvent wash, after each capping step too, a solvent wash takes place which is equivalent to about 40 column volumes of the solvent. Considering that about 212 column volumes of the solvent wash is done for a given synthesis run, about 19% of the wash solvent is used for the capping steps. Each capping step takes between 3-6 minutes. This corresponds to about 8% of the overall synthesis time including the 13 cycles and DEA treatment.

```
imetelstat and imetelstat sodium
                                    SEQ ID NO: 1
    5'-R-TAGGGTTAGACAA-NH₂-3'
``` wherein R represents palmitoyl [$(CH_2)_{14}CH_3$] amide is conjugated through an aminoglycerol linker to the 5'-thiophosphate group of an N3→P5' thiophosphoramidate (NPS)-linked oligonucleotide.

The invention claimed is:

1. A method of synthesizing the N3'→P5' thiophosphoramidate oligonucleotide imetelstat of formula

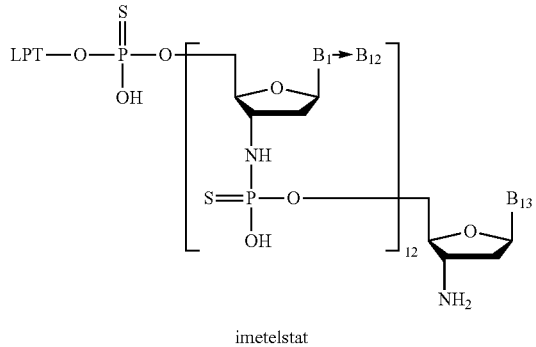

imetelstat

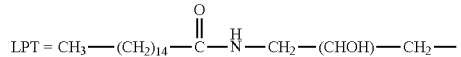

$B_1$ = T
$B_2$ = A
$B_3$ = G
$B_4$ = G
$B_5$ = G
$B_6$ = T
$B_7$ = T
$B_8$ = A
$B_9$ = G
$B_{10}$ = A
$B_{11}$ = C
$B_{12}$ = A
$B_{13}$ = A
T = thymine
A = adenine
G = guanine
C = cytosine the method comprises of a) providing a first 3'-amino protected nucleotide attached to a solid-phase support of formula (A) wherein PG is an acid-labile protecting group;

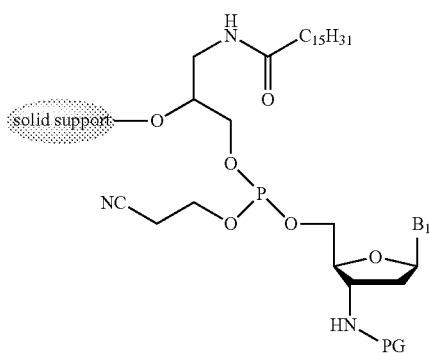

b) deprotecting the protected 3'-amino group to form a free 3'-amino group;

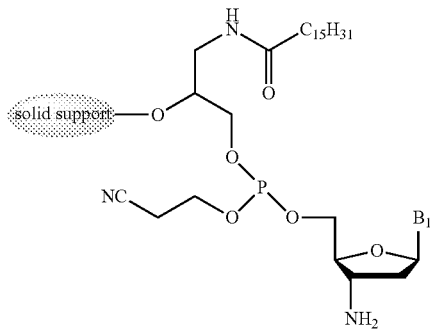

c) reacting the free 3'-amino group with a protected 3'-aminonucleoside-5'-O-cyanoethyl-N,N-diisopropylaminophosphoramidite monomer of formula ($B'_n$) wherein n=2 to form an internucleoside N3'→P5'-phosphoramidite linkage;

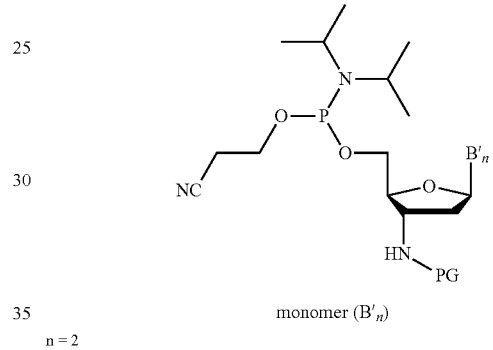

monomer ($B'_n$)
n = 2 d) sulfurization of the internucleoside phosphoramidite group using an acyl disulfide to form a N3'→P5' thiophosphoramidate;

e) repeating 11 times in successive order the deprotection step b), the coupling step c) with a protected 3'-aminonucleoside-5'-O-cyanoethyl-N,N-diisopropylaminophosphoramidite monomer of formula ($B'_n$) wherein the protected nucleoside base B' in monomer ($B'_n$) is successively the protected nucleobase $B_3$ to $B_{13}$ in the respective 11 coupling steps, and the sulfurization step d);

f) removing the acid-labile protecting group PG; and g) cleaving and deprotecting imetelstat from the solid-phase support;

characterized in that no additional capping step is performed in any of the reaction steps a) to e).

2. The method as claimed in claim 1 wherein imetelstat is further converted into its sodium salt.

3. The method as claimed in claim 1 wherein the acyl disulfide is selected from dibenzoyl disulphide, bis(phenylacetyl) disulfide (PADS), bis(4-methoxybenzoyl) disulphide, bis(4-methylbenzoyl) disulphide, bis(4-nitrobenzoyl) disulphide and bis(4-chlorobenzoyl) disulfide.

4. The method as claimed in claim 3 wherein the acyl disulfide is PADS.

5. The method as claimed in claim 4 wherein PADS is dissolved in a mixture of 3-picoline or 2,6-lutidine with a co-solvent selected from acetonitrile, toluene, 1-methylpyrrolidinone and tetrahydrofuran.

6. The method as claimed in claim 5 wherein PADS is dissolved in a mixture of 2,6-lutidine with acetonitrile.

7. The method as claimed in claim 6 wherein the PADS solution is aged between 4 and 14 hours before use.

8. The method as claimed in claim 1 wherein the acid-labile protecting group PG is selected from triphenylmethyl, p-anisyldiphenylmethyl, and di-p-anisylphenylmethyl.

9. The method as claimed in claim 1 wherein the acid-labile protecting group PG is removed by treatment with an acidic solution.

10. The method as claimed in claim 1 wherein the protecting group on the adenine, cytosine and guanine base in the monomer of formula ($B'_n$) is a base-labile protecting group selected from acetyl, benzoyl, isobutyryl, dimethylformamidinyl, and dibenzylformamidinyl.

11. The method as claimed in claim 1 wherein the coupling step c) is performed using an activator selected from tetrazole, 5-(ethylthio)-1H-tetrazole, 5-(4-nitro-phenyl)tetrazole, 5-(2-thienyl)-1H-tetrazole, triazole, and pyridinium chloride.

12. The method as claimed in claim 1 wherein step f) is performed by treatment with a basic solution.

13. The method as claimed in claim 12 wherein the basic solution is diethylamine dissolved in acetonitrile or aqueous ammonia dissolved in an alcohol, or a combination of both.

\* \* \* \* \*

UNITED STATES PATENT AND TRADEMARK OFFICE
CERTIFICATE OF CORRECTION

PATENT NO. : 11,332,489 B2
APPLICATION NO. : 16/623984
DATED : May 17, 2022
INVENTOR(S) : Jale Muslehiddinoglu et al.

Page 1 of 1

It is certified that error appears in the above-identified patent and that said Letters Patent is hereby corrected as shown below:

In the Claims

In Column 23, Line 21, please replace "step f)" with -- step g) --

Signed and Sealed this
Fifth Day of July, 2022

Katherine Kelly Vidal
*Director of the United States Patent and Trademark Office*